(12) United States Patent
Rhodes

(10) Patent No.: US 8,216,319 B2
(45) Date of Patent: Jul. 10, 2012

(54) METHOD OF REPAIRING A KNEE JOINT

(75) Inventor: James M. Rhodes, Warsaw, IN (US)

(73) Assignee: Depuy Products, Inc., Warsaw, IN (US)

( * ) Notice: Subject to any disclaimer, the term of this patent is extended or adjusted under 35 U.S.C. 154(b) by 826 days.

(21) Appl. No.: 11/259,985

(22) Filed: Oct. 27, 2005

(65) Prior Publication Data

US 2007/0100459 A1  May 3, 2007

(51) Int. Cl.
*A61F 2/28* (2006.01)
(52) U.S. Cl. .................................... 623/20.15
(58) Field of Classification Search ..... 623/20.14–20.36
See application file for complete search history.

(56) References Cited

U.S. PATENT DOCUMENTS

| | | | | |
|---|---|---|---|---|
| 3,715,763 A | * | 2/1973 | Link ........................ | 623/20.3 |
| 3,748,662 A | * | 7/1973 | Helfet ...................... | 623/20.31 |
| 3,774,244 A | * | 11/1973 | Walker ..................... | 623/20.3 |
| 3,806,961 A | * | 4/1974 | Muller ..................... | 623/20.19 |
| 3,852,830 A | | 12/1974 | Marmor | |
| 3,878,566 A | * | 4/1975 | Bechtol .................... | 623/20.19 |
| 3,953,889 A | | 4/1976 | Scieszinski et al. | |
| 3,953,899 A | | 5/1976 | Charnley | |
| 4,034,418 A | | 7/1977 | Jackson et al. | |
| 4,151,615 A | * | 5/1979 | Hall ......................... | 623/20.19 |
| 4,178,641 A | * | 12/1979 | Grundei et al. ........... | 623/20.31 |
| 4,224,696 A | | 9/1980 | Murray et al. | |
| 4,224,697 A | | 9/1980 | Murray et al. | |
| 4,261,064 A | * | 4/1981 | Helfet ...................... | 623/20.31 |
| 4,340,978 A | | 7/1982 | Buechel et al. | |
| 4,838,891 A | * | 6/1989 | Branemark et al. ...... | 623/20.3 |
| 5,037,439 A | * | 8/1991 | Albrektsson et al. ..... | 623/20.3 |
| 5,108,441 A | * | 4/1992 | McDowell ................ | 128/898 |
| 5,123,927 A | * | 6/1992 | Duncan et al. ........... | 623/20.21 |
| 5,263,987 A | | 11/1993 | Shah | |
| 5,632,745 A | | 5/1997 | Schwartz | |
| 5,702,458 A | | 12/1997 | Burstein et al. | |
| 5,749,874 A | | 5/1998 | Schwartz | |
| 5,759,190 A | | 6/1998 | Vice-Hansen et al. | |
| 5,769,899 A | | 6/1998 | Schwartz et al. | |
| 5,871,541 A | | 2/1999 | Gerber | |
| 5,906,577 A | | 5/1999 | Beane et al. | |
| 5,906,596 A | | 5/1999 | Tallarida | |
| 6,123,728 A | | 9/2000 | Brosnahan et al. | |

(Continued)

FOREIGN PATENT DOCUMENTS

DE  2933174 A1  4/1980

(Continued)

OTHER PUBLICATIONS

Search Report, EP1779813A1.

(Continued)

*Primary Examiner* — David Isabella
*Assistant Examiner* — Ann Schillinger

(57) ABSTRACT

A knee joint is repaired by implanting a trochlear implant component, a patellar implant component and an anti-abrasion stud. The stud has a bearing surface, a bone-facing surface and a fixation post. The fixation post is implanted in the distal femur so that the bearing surface of the stud stands above the patient's native articular cartilage. The stud and trochlear component are implanted in close enough proximity to limit contact between the patellar component and the native articular cartilage around the trochlear component during flexion and extension of the knee joint.

14 Claims, 13 Drawing Sheets

U.S. PATENT DOCUMENTS

| | | | |
|---|---|---|---|
| 6,132,468 A * | 10/2000 | Mansmann | 623/20.16 |
| 6,142,936 A | 11/2000 | Beane et al. | |
| 6,171,340 B1 * | 1/2001 | McDowell | 623/18.11 |
| 6,251,143 B1 | 6/2001 | Schwartz et al. | |
| 6,352,558 B1 | 3/2002 | Spector | |
| 6,428,577 B1 | 8/2002 | Evans et al. | |
| 6,440,063 B1 | 8/2002 | Beane et al. | |
| 6,468,314 B2 | 10/2002 | Schwartz et al. | |
| 6,520,964 B2 * | 2/2003 | Tallarida et al. | 606/71 |
| 6,527,754 B1 | 3/2003 | Tallarida et al. | |
| 6,616,696 B1 * | 9/2003 | Merchant | 623/20.18 |
| 6,626,945 B2 | 9/2003 | Simon et al. | |
| 6,626,950 B2 | 9/2003 | Brown et al. | |
| 6,660,039 B1 | 12/2003 | Evans et al. | |
| 6,679,917 B2 | 1/2004 | Elk | |
| 6,702,821 B2 | 3/2004 | Bonutti | |
| 6,709,460 B2 | 3/2004 | Merchant | |
| 6,712,856 B1 * | 3/2004 | Carignan et al. | 623/20.35 |
| 6,712,865 B2 * | 3/2004 | Lu | 44/275 |
| 6,783,550 B2 * | 8/2004 | MacArthur | 623/20.14 |
| 7,258,701 B2 * | 8/2007 | Aram et al. | 623/20.15 |
| 2001/0010023 A1 | 7/2001 | Schwartz et al. | |
| 2001/0039455 A1 * | 11/2001 | Simon et al. | 623/23.51 |
| 2002/0055783 A1 * | 5/2002 | Tallarida et al. | 623/20.14 |
| 2002/0099446 A1 * | 7/2002 | MacArthur | 623/20.14 |
| 2002/0120274 A1 | 8/2002 | Overaker et al. | |
| 2002/0173855 A1 | 11/2002 | Mansmann | |
| 2003/0004578 A1 | 1/2003 | Brown et al. | |
| 2003/0036801 A1 | 2/2003 | Schwartz et al. | |
| 2003/0060887 A1 * | 3/2003 | Ek | 623/20.14 |
| 2003/0220700 A1 | 11/2003 | Hammer et al. | |
| 2005/0064042 A1 | 3/2005 | Vunjak-Novakovic et al. | |
| 2005/0107884 A1 * | 5/2005 | Johnson et al. | 623/20.15 |
| 2005/0154471 A1 | 7/2005 | Aram et al. | |
| 2005/0177242 A1 | 8/2005 | Lotke | |

FOREIGN PATENT DOCUMENTS

| | | |
|---|---|---|
| EP | 0170779 B1 | 6/1988 |
| GB | 1522497 A | 8/1978 |
| JP | 2002272756 | 9/2002 |
| WO | WO 95/24874 A1 | 9/1995 |
| WO | WO 95/30388 A1 | 11/1995 |
| WO | WO 96/24302 A1 | 8/1996 |
| WO | WO 96/24304 A1 | 8/1996 |
| WO | WO 97/25942 A1 | 7/1997 |
| WO | WO 00/74554 A2 | 12/2000 |
| WO | WO 2004/103224 A1 | 12/2004 |

OTHER PUBLICATIONS

F.M. Hall and G. Wyshak, "Thickness of Articular Cartilage in the Normal Knee" J Bone Joint Aurg Am. 1980; p. 411, Table 1; 62:408-413; The Journal of Bone and Joint Surgery, Needham, MA.

J. Bern Jordan, "Comparison of Four Treatments for Patients with Severe Knee Cartilage Damage," Jun. 17, 2001, http://tc.engr.wisc.edu/UER/uer01/author1/content.html; Technical Communication Program, University of Wisconsin, Madison, Wisconsin.

Arciero, Major and Toomey, "Patellofemoral Arthroplasty: A Three-to-Nine Year Follow-Up Study," 236 Clinical Orthopaedics and Related Research, vol. 236, Nov. 1, 1988, pp. 60-71.

Bourne, Rorabeck, Finlay and Nott, "Kinematic I and Oxford Knee Arthroplasty: A 5-8-year Follow-up Study," The Journal of Arthroplasty, vol. 2, No. 4, Dec. 1987, pp. 285-291.

Shoji, D'Ambrosia and Lipscomb, "Failed Polycentric Total Knee Prostheses," The Journal of Bone and Joint Surgery, vol. 58-A, No. 6, Sep. 1976, pp. 773-777.

Stockley, Douglas and Elson, "Bicondylar St. Georg Sledge Knee Arthroplasty," Clinical Orthopaedics and Related Research, No. 255, Jun. 1990, pp. 228-234.

Biomet, Oxford, Biomet, Warsaw, Indiana.

Depuy Orthopaedics, LCS® PFJ Prosthesis, DePuy Orthopaedics, Warsaw, Indiana.

Depuy Orthopaedics, LCS® UNI Unicompartmental Knee System, DePuy Orthopaedics, Warsaw, Indiana.

Depuy Orthopaedics, Preservation™ Uni-Compartmental Knee, DePuy Orthopaedics, Warsaw, Indiana.

Dervin, MD, FRCSC, Geoffrey F., et al., Effect of Arthroscopic Debridement for Osteoarthritis of the Knee on Health-Related Quality of Life, The Journal of Bone & Joint Surgery, Jan. 2003, pp. 10-19, vol. 85-A, No. 1.

Hsieh, M.D., Po-Ching, et al., Repair of Full-Thickness Cartilage Defects in Rabbit Knees With Free Periosteal Graft Preincubated With Transforming Growth Factor, Orthopedics, Apr. 2003, pp. 393-402, vol. 26, No. 4.

Mainil-Varlet, MD, Phd, Pierre, et al., Histological Assessment of Cartilage Repair, The Journal of Bone & Joint Surgery, 2003, pp. 45-57, vol. 85-A, Supplement 2.

O'Driscoll, Ph.D., M.D., F.R.C.S., Shawn W., Current Concepts Review—The Healing and Regeneration of Articular Cartilage, The Journal of Bone & Joint Surgery, Dec. 1998, pp. 1795-1812, vol. 80-A, No. 12.

Shelbourne, MD, K. Donald, et al., Outcome of Untreated Traumatic Articular Cartilage Defects of the Knee, The Journal of Bone & Joint Surgery, 2003, pp. 8-16, vol. 85-A, Supplement 2.

Smith & Nephew Richards, Patella MOD III, Smith & Nephew Richards, Memphis Tennessee.

Waldman, Phd, Stephen D., et al., Effect of Biomechanical Conditioning on Cartilaginous Tisse Formation in Vitro, The Journal of Bone & Joint Surgery, 2003, pp. 101-105, vol. 85-A, Supplement 2.

Response—Dec. 22, 2009—U.S. Appl. No. 11/260,386.

Non-Final Rejection—Sep. 29, 2009—U.S. Appl. No. 11/260,386.

Restriction Requirement—Jan. 21, 2009—U.S. Appl. No. 11/260,386.

Mechanical Testing of Bone and the Bone-Implant Interface, edited by Yuehuei H. An, M.D. and Robert A. Draughn, D. Sc., CRC Press 2000.

Brown, Thomas D. and Vrahas, Mark S., "The Apparent Elastic Modulus of the Juxtarticular Subchondral Bone of the Femoral Head," 2 J. Orthop. Res. 1984 pp. 32-38.

* cited by examiner

METHOD OF REPAIRING A KNEE JOINT

FIELD OF THE INVENTION

This invention relates generally to prostheses for human body joints, and more particularly, to prostheses for human knees and to methods of repairing knee joints using prostheses.

BACKGROUND OF THE INVENTION

When a human skeletal joint is damaged, whether as a result of an accident or illness, a prosthetic replacement of the damaged joint may be necessary to relieve pain and to restore normal use to the joint. Typically the entire joint is replaced by means of a surgical procedure that involves removal of the ends of the corresponding damaged bones and replacement of these ends with prosthetic implants. This replacement of a native joint with a prosthetic joint is referred to as a primary total-joint arthroplasty.

For a damaged human knee, the total knee is commonly replaced with prosthetic components shaped to replace portions of the distal femur, proximal tibia and patella. Prosthetic components for use in replacing the distal femur are shaped to replace the articulating surfaces (shown at 21, 23 in FIG. 1) of the medial condyle (shown at 20 in FIG. 1), lateral condyle (shown at 22 in FIG. 1) and trochlea, and prosthetic components for use in replacing the proximal tibia are shaped to replace the tibial plateau. Commonly, the tibial component is two piece: one piece is affixed to the bone and the other piece is a bearing with concave surfaces receiving the femoral condyles. Frequently, a portion of the patella is also replaced with a prosthetic component as part of the total knee replacement.

In some patients, only a portion of the knee is damaged or injured. For such patients, individual compartments of the knee may be replaced. For example, the medial or lateral compartment of the knee may be replaced with uni-condylar components that replace the articulating surface of one condyle of the distal femur and one side of the tibial plateau. The patellofemoral compartment may be replaced with a femoral component that replaces a portion of the trochlea and a patellar component that replaces part of the patella. In some instances, two or three unicompartmental components are implanted together in one joint; for example, two sets of uni-condylar components could be implanted together to replace the articulating surfaces of both the medial and lateral sides of the tibio-femoral joint, a trochlear component (and patellar component) and a set of uni-condylar femoral and tibial components could be implanted together, or two sets of uni-condylar components and a trochlear component (and patellar component) could be implanted together. The following journal articles report, among other things: use of patellofemoral components (trochlear component and patellar component) and one or two sets of uni-condylar components, Arciero, Major and Toomey, "Patellofemoral Arthroplasty: A Three-to-Nine Year Follow-Up Study," 236 Clinical Orthopaedics and Related Research, Vol. 236, Nov. 1, 1988, pages 60-71; and two sets of uni-condylar components, Bourne, Rorabeck, Finlay and Nott, "Kinematic I and Oxford Knee Arthroplasty: A 5-8-year Follow-up Study," The Journal of Arthroplasty, Vol. 2, No. 4, December, 1987, pages 285-291, and Shoji, D'Ambrosia and Lipscomb, "Failed Polycentric Total Knee Prostheses," The Journal of Bone and Joint Surgery, Vol. 58-A, No. 6, September 1976, pages 773-777, and Stockley, Douglas and Elson, "Bicondylar St. Georg Sledge Knee Arthroplasty," Clinical Orthopaedics and Related Research, No. 255, June, 1990, pages 228-234.

Patents and published applications related to uni-condylar knee implant components or patellofemoral implant components include the following: U.S. Pat. No. 3,852,830; U.S. Pat. No. 3,953,889; U.S. Pat. No. 4,034,418; U.S. Pat. No. 4,340,978; U.S. Pat. No. 4,838,891; U.S. Pat. No. 5,871,541; U.S. Pat. No. 6,616,696; and U.S. Pat. No. 6,709,460.

Commercial uni-condylar knee implant components or patellofemoral implant components include the LCS® UNI Unicompartmental Knee System (DePuy Orthopaedics, Warsaw, Ind.), the Preservation™ Uni-Compartmental Knee (DePuy Orthopaedics, Warsaw, Ind.), the LCS® PFJ Prosthesis (DePuy Orthopaedics, Warsaw, Ind.), the Patella MOD III and Patella II (Smith & Nephew/Richards) and the Oxford (Biomet).

When knees are replaced with common total joint prostheses, substantially all of the potential articulating surface of the distal femur is replaced and covered with metal; no native articular cartilage remains exposed in the potential area of articulation. In contrast, when one or more compartments of a knee are replaced with unicompartmental components, substantial areas of native cartilage are not covered by metal, and remain exposed. FIG. 1 illustrates an example of a human femur 10 with an implanted trochlear implant component 11. FIG. 2 illustrates an example of a human femur 10 with an implanted trochlear implant component 11 replacing the articulating surface of the trochlea together with a uni-condylar femoral component 13 replacing the articulating surface of one of the femoral condyles. In FIG. 2, the areas of exposed native tissue include the intercondylar notch 16, and areas 18, 19 of the distal femoral condyles 20, 22 adjacent to the intercondylar notch 16 and an area 24 of the distal femoral condyles 20, 22 lying between the distal portion 27 of the trochlear component 11 and the anterior portion 29 of the uni-condylar femoral component 13. As shown in FIGS. 1-2, the distal portion 26 of the trochlear component 11 generally tapers toward its distal end, which is positioned near or within the intercondylar notch 16.

FIG. 3 illustrates the femur 10 of FIG. 2, shown with a patellar implant component 31 engaging the trochlear component 11. The patellar component 31 includes a bearing surface 33 that bears against a bearing surface 35 of the trochlear component 11. The exposed bearing surface 35 of the illustrated trochlear implant component 11 has two convex surfaces 39, 41 meeting along a groove 43. FIG. 4 illustrates the femur of FIG. 3 with the patellar component 31 positioned with respect to the trochlear component 11 as it would be with the knee in deep flexion. When the knee is in deep flexion, a portion of the patellar component 31 may extend beyond the edges of the distal portion 27 of the trochlear component 11. Such an overhanging portion (shown at 37 in FIG. 4) of the patellar component 31 may contact and rub against the patient's native tissue (such as native tissue indicated at 18, 19 and 24 in FIG. 4) as the knee flexes and extends. This contact may result in painful irritation of the native tissue. This painful irritation could be prevented through use of a total knee prosthesis; however, use of a total knee prosthesis could result in an unnecessary loss of healthy bone tissue. The pain resulting from this irritation could be treated by revising the surgery, replacing the uni-compartmental components 11, 13 with a total knee prosthesis, again resulting in the loss of healthy bone tissue. A need exists for a means for preventing or treating the patient's native tissue near the intercondylar notch without requiring the removal and replacement of healthy tissue.

U.S. Pat. Publication No. 2005/0177242 A1, entitled "Patello-Femoral Prosthesis," discloses a trochlear component with an intercondylar notch portion with tapered wings extending distally and curved posteriorly. The wings also curve away from each other in the posterior direction. Although the wings provide additional bearing surfaces for the patellar implant component, they may not cover the portions of the femur that potentially contact the patellar prosthesis-bearing surface. In addition, individual patient anatomies may prevent use of such a trochlear implant in all patients.

SUMMARY OF THE INVENTION

The present invention provides an implant system and surgical technique that protects a patient's native tissue when the patient has been treated with uni-compartmental or multi-compartmental arthroplasty. The protection offered by the present invention can be provided in a wide range of patient anatomies.

In one aspect, the present invention provides a method of repairing a knee joint. A trochlear component is implanted on the distal femur. The trochlear component has a proximal and a distal end. A patellar component is implanted on the patella. A stud is provided; the stud has a bearing surface, a bone-facing surface and a fixation post extending outward from the bone-facing surface. The fixation post of the stud is implanted in the distal femur so that the bearing surface of the stud stands above the native articular cartilage. The stud and trochlear component are implanted in close enough proximity to limit contact between the patellar component and the native articular cartilage around the trochlear component during flexion and extension of the knee joint.

BRIEF DESCRIPTION OF THE DRAWINGS

FIG. 111 is a top plan view of the anti-abrasion stud of FIGS. 7-10;

DETAILED DESCRIPTION

The present invention provides an orthopaedic implant system that includes, in addition to uni-compartmental implant components, one or more anti-abrasion studs 50 that extend the bearing areas of other implant components to protect native tissue from damage resulting from engaging a patellar implant component during flexion and extension. In addition to the anti-abrasion studs 50, the orthopaedic implant system of the present invention may include a trochlear implant component, a patellar implant component, one or more uni-condylar femoral implant components, and one or more uni-condylar tibial implant components against which the uni-condylar femoral components articulate.

Figure 5:
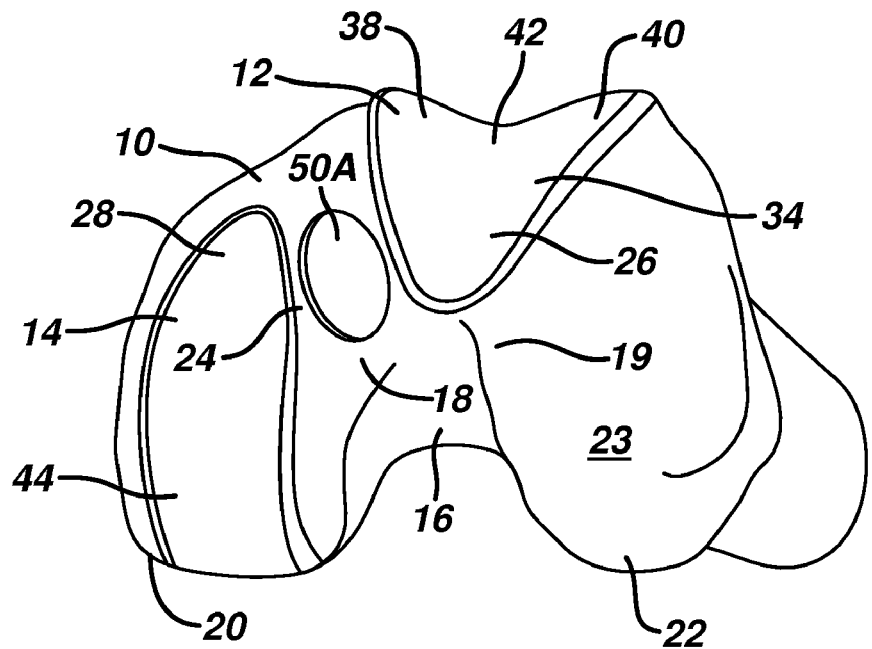
FIG. 5 is a perspective view of a distal femur, similar to FIG. 2, but with a first embodiment of a stud implanted in the space between a trochlear component and uni-condylar implant component.

FIG. 5 illustrates the distal end of a human femur 10, shown with two compartments of the distal femur 10 replaced by a trochlear implant component and a uni-condylar femoral implant component. The illustrated trochlear and uni-condy-lar implant components of FIG. 5. are similar to those disclosed in U.S. Pat. App. Publication No. 2005/0154471 A1, entitled "Systems and Methods for Compartmental Replacement in a Knee," which is incorporated by reference herein in its entirety. However, it should be understood that the present invention is not limited to the structures disclosed in that patent application; the principles of the present invention, and the addition of anti-abrasion studs 50, can be broadly applied to other implant systems wherein a portion of native tissue is exposed to potential contact with the articulating surface.

The illustrated trochlear implant component 12 is sized and shaped to replace a portion of the patellofemoral compartment of the distal femur without covering the distal articulating surfaces 21, 23 of the medial and lateral condyles 20, 22. The trochlear component 12 has an exposed bearing surface 34 and a bone-facing surface underlying the bearing surface. The exposed bearing surface 34 of the illustrated trochlear implant component 12 has two convex surfaces 38, 40 meeting along a groove 42. The illustrated trochlear implant component 12 is sized and shaped to provide an articulating surface for the patellar component 30, so that the patellar component 30 engages the trochlear component 12 when the leg is in extension as well as through a normal range of flexion.

The illustrated uni-condylar implant component 14 is sized and shaped to replace the femoral condyle surface 21 that articulates with the proximal tibia. The uni-condylar femoral implant component 14 has an exposed arcuate articulating or bearing surface 44 and an underlying bone-facing surface. The bone-facing surface can be porous to promote bone ingrowth, or can be adapted for cemented fixation. Overall, the illustrated uni-condylar femoral implant component 14 is sized and shaped to cover the distal and posterior articulating surfaces of one femoral condyle.

Figure 4:
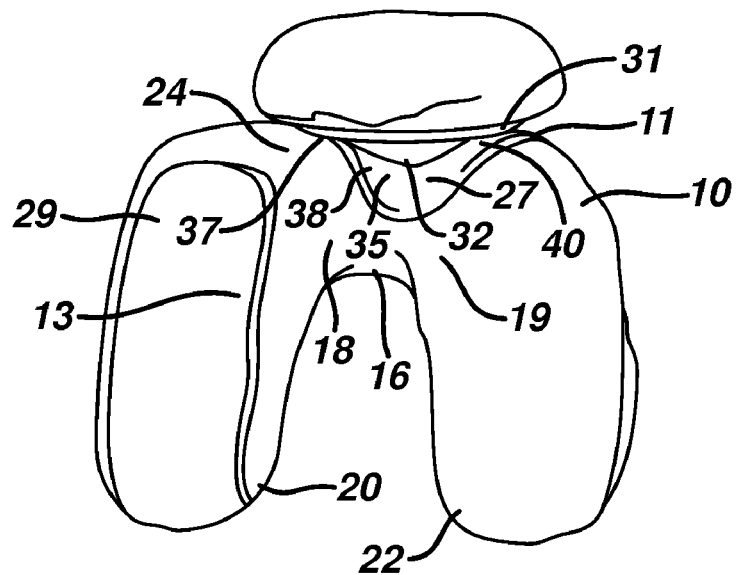
FIG. 4 is an end view of a distal femur, illustrating a possible position of the patella and prior art patellar implant with respect to a prior art trochlear component and prior art uni-condylar femoral component, and further illustrating the potential for the patellar implant component to contact native tissue during flexion and extension of the knee.
Figure 6:
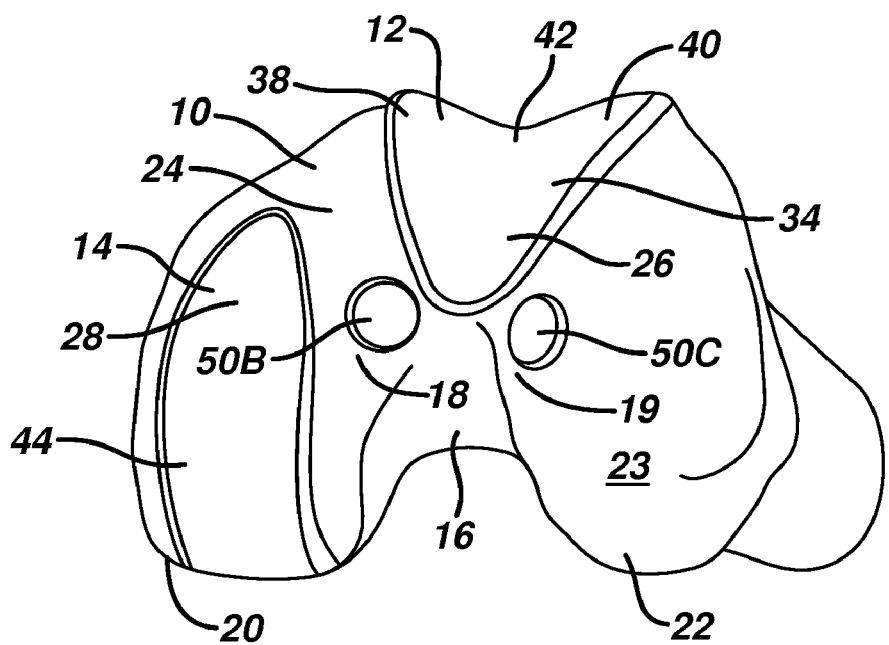
FIG. 6 is a perspective view of a distal femur, similar to FIGS. 2 and 5, but with two studs of a second embodiment implanted in areas adjacent to the intercondylar notch of the femur.
Figure 7:
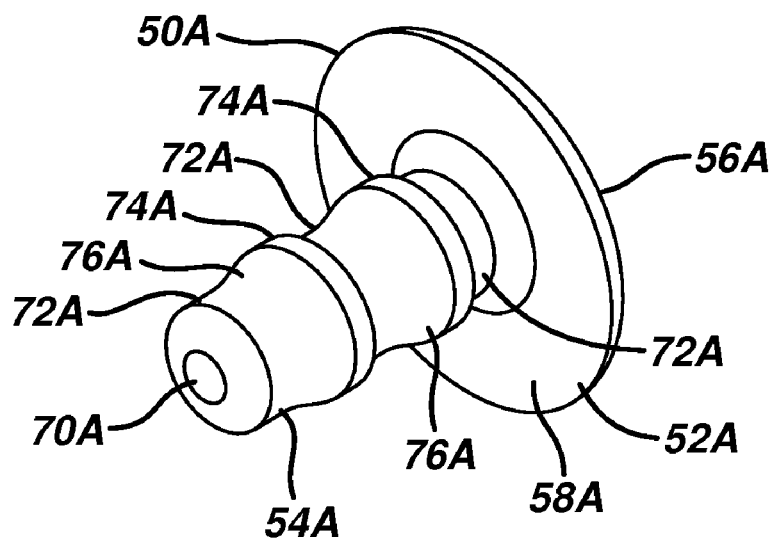
FIG. 7 is perspective view of a first embodiment of an anti-abrasion stud.
Figure 8:
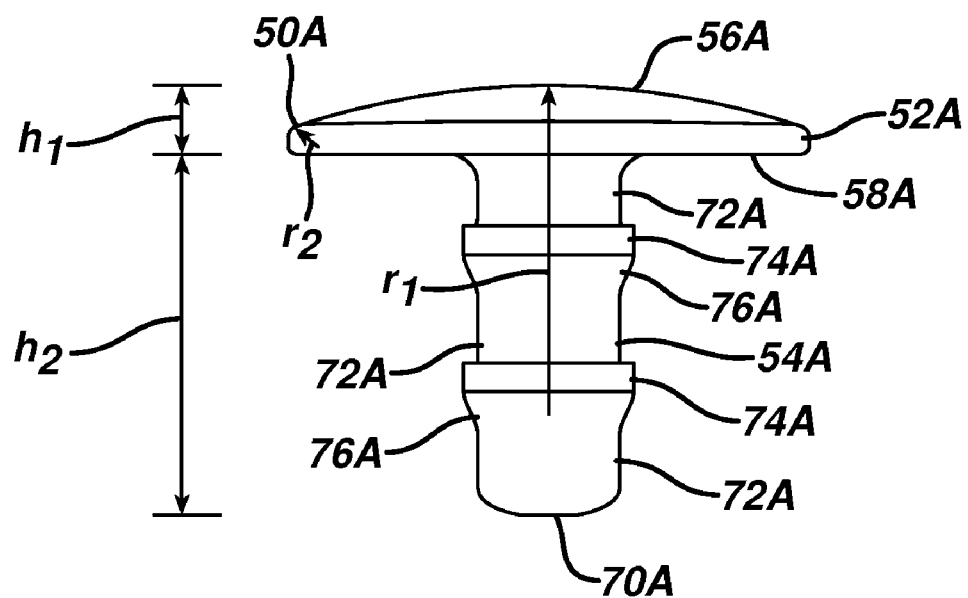
FIG. 8 is an elevation of the anti-abrasion stud of FIG. 7.
Figure 9:
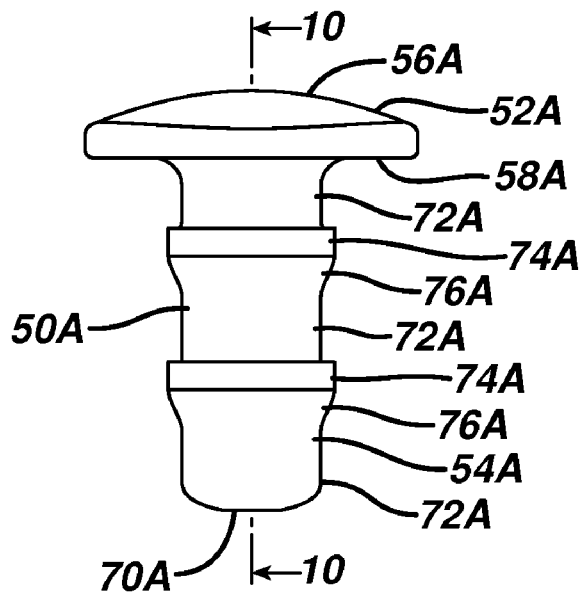
FIG. 9 is a second elevation of the anti-abrasion stud of FIGS. 7-8.
Figure 10:
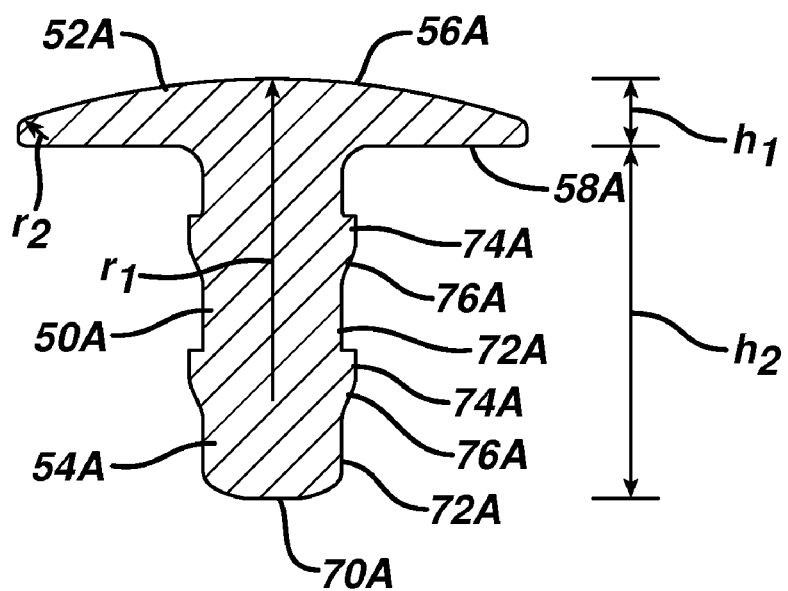
FIG. 10 is a cross-section of the anti-abrasion stud of FIG. 9, taken along line 10-10 of FIG. 9.
Figure 11:
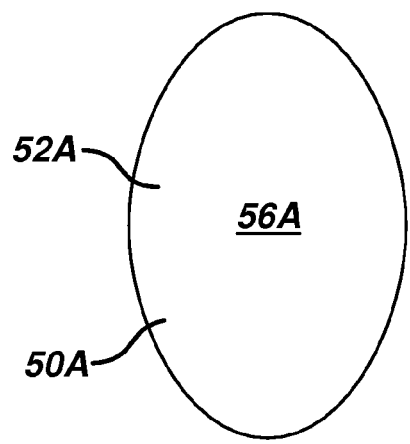
Figure 12:
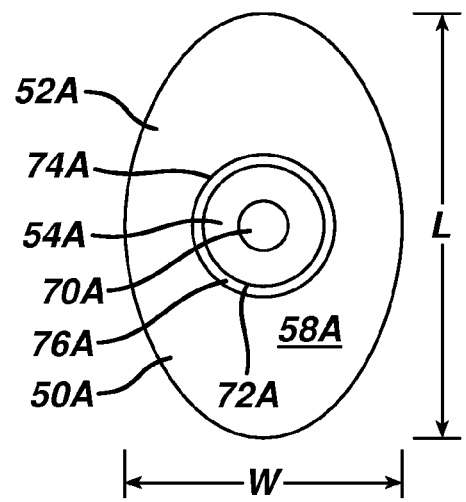
FIG. 12 is a bottom plan view of the anti-abrasion stud of FIGS. 7-11.
Figure 13:
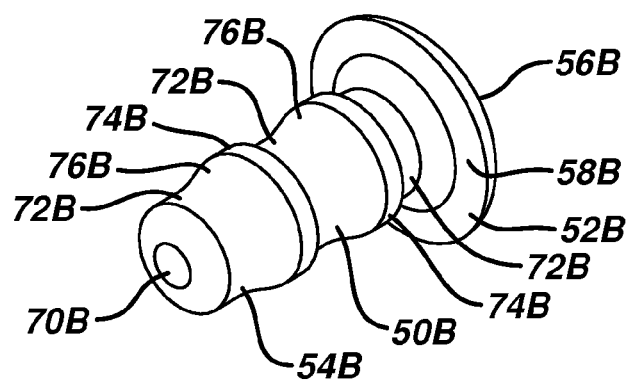
FIG. 13 is perspective view of a second embodiment of an anti-abrasion stud.
Figure 14:
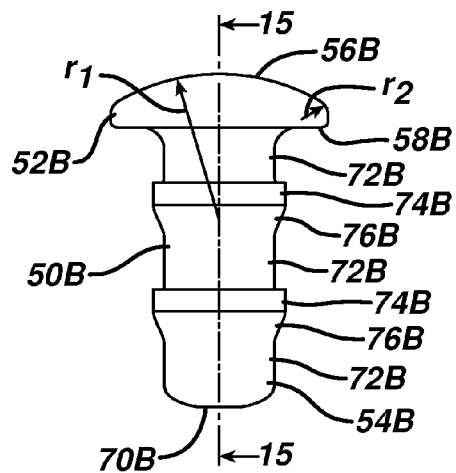
FIG. 14 is an elevation of the anti-abrasion stud of FIG. 13.
Figure 15:
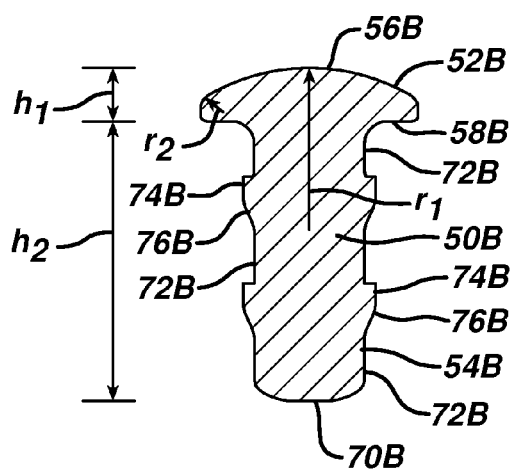
FIG. 15 is a cross-section of the anti-abrasion stud of FIG. 14, taken along line 15-15 of FIG. 14.
Figure 16:
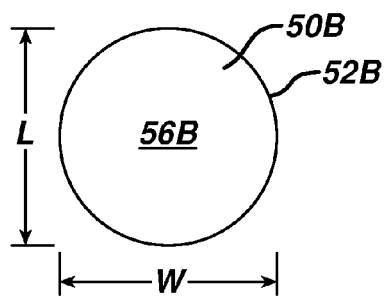
FIG. 16 is a top plan view of the anti-abrasion stud of FIGS. 13-15.
Figure 17:
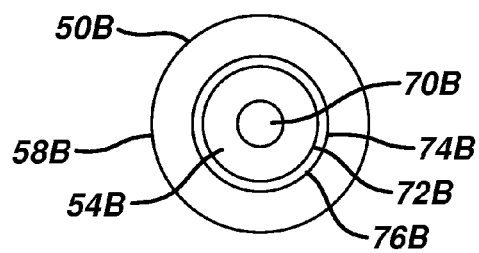
FIG. 17 is a bottom plan view of the anti-abrasion stud of FIGS. 13-16.
Figure 18:
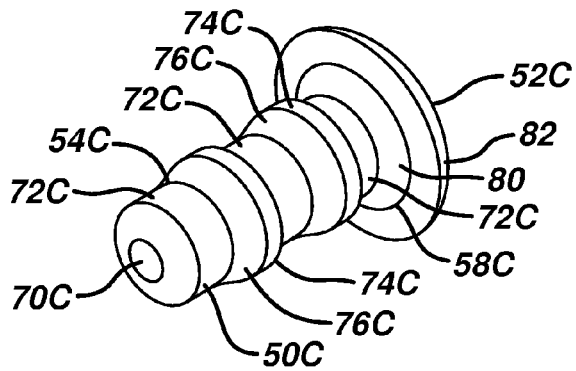
FIG. 18 is perspective view of a third embodiment of an anti-abrasion stud.
Figure 19:
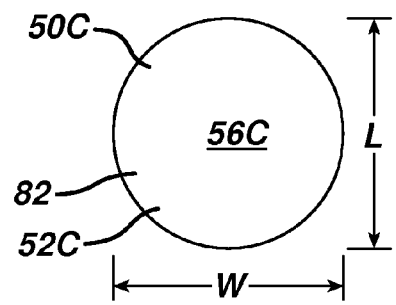
FIG. 19 is a top plan view of the anti-abrasion stud of FIG. 18.
Figure 20:
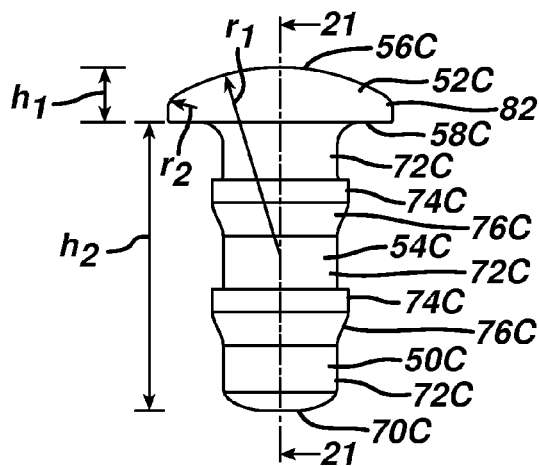
FIG. 20 is an elevation of the anti-abrasion stud of FIGS. 18-19.
Figure 21:
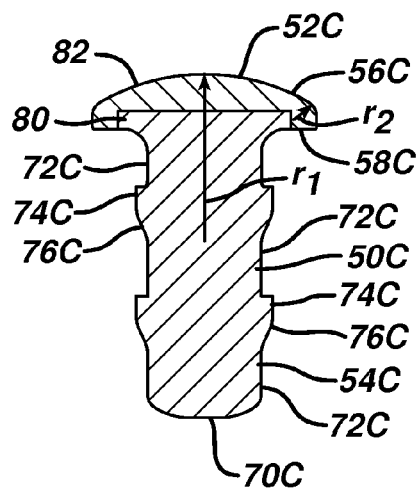
FIG. 21 is a cross-section of the anti-abrasion stud of FIGS. 18-20, taken along line 21-21 of FIG. 20.
Figure 22:
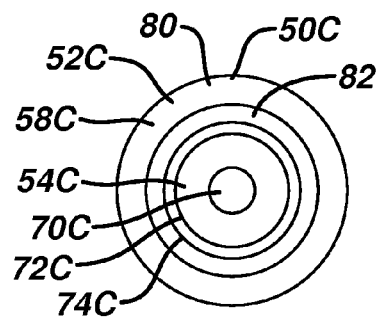
FIG. 22 is a bottom plan view of the anti-abrasion stud of FIGS. 18-21.
Figure 23:
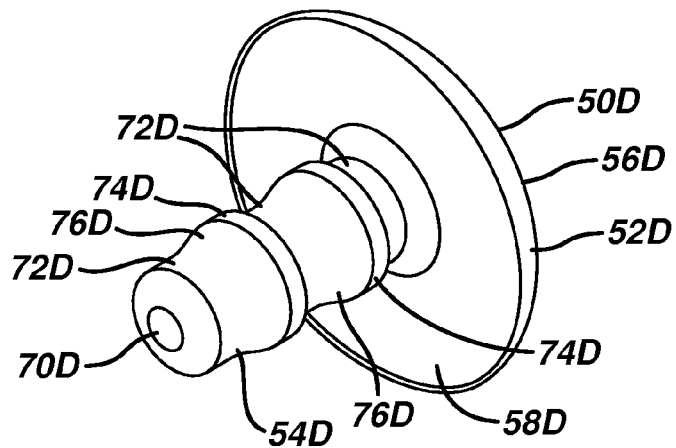
FIG. 23 is perspective view of a fourth embodiment of an anti-abrasion stud.
Figure 24:
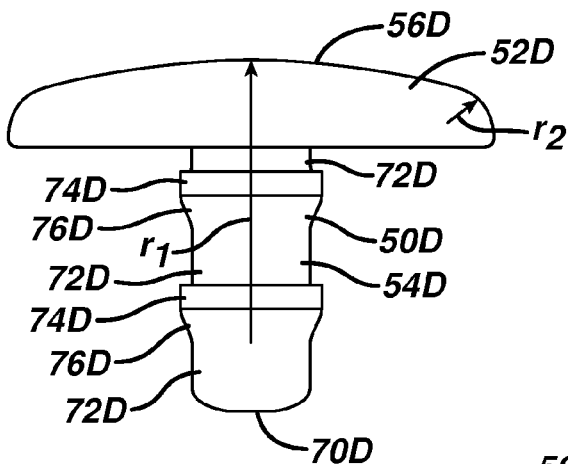
FIG. 24 is an elevation of the anti-abrasion stud of FIG. 23.
Figure 25:
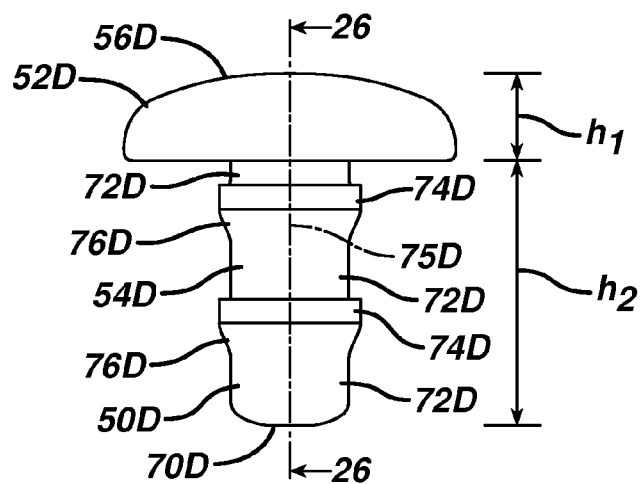
FIG. 25 is a second elevation of the anti-abrasion stud of FIGS. 23-24.
Figure 26:
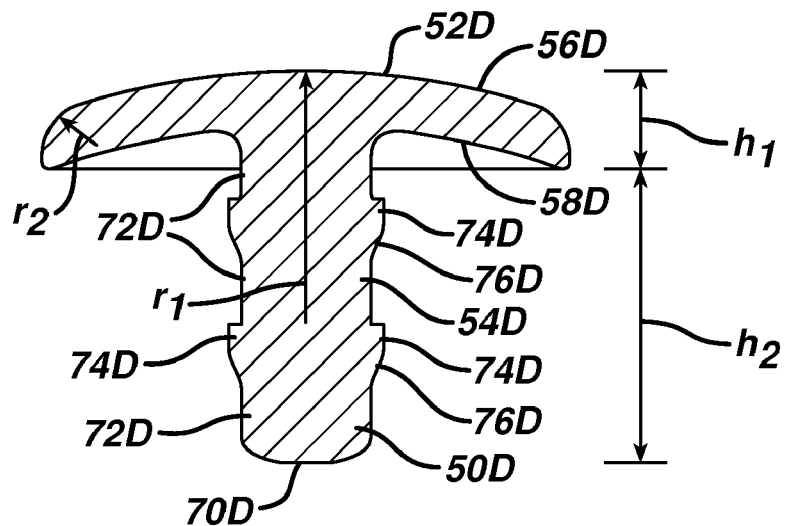
FIG. 26 is a cross-section of the anti-abrasion stud of FIGS. 23-25, taken along line 26-26 of FIG. 25.
Figure 27:
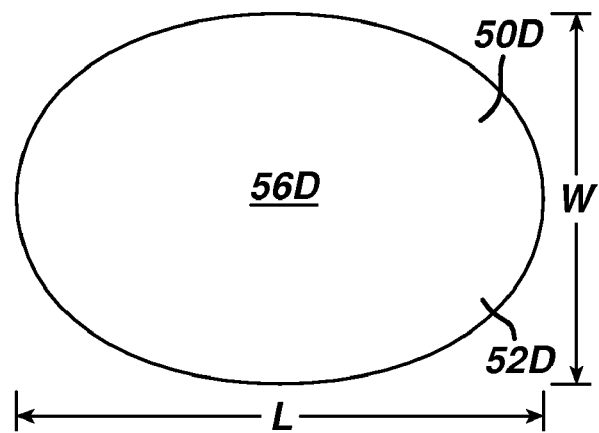
FIG. 27 is a top plan view of the anti-abrasion stud of FIGS. 23-26.
Figure 28:
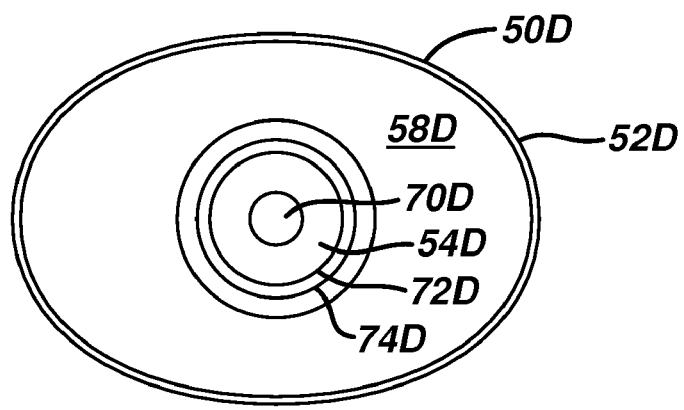
FIG. 28 is a bottom plan view of the anti-abrasion stud of FIGS. 23-27.
Figure 29:
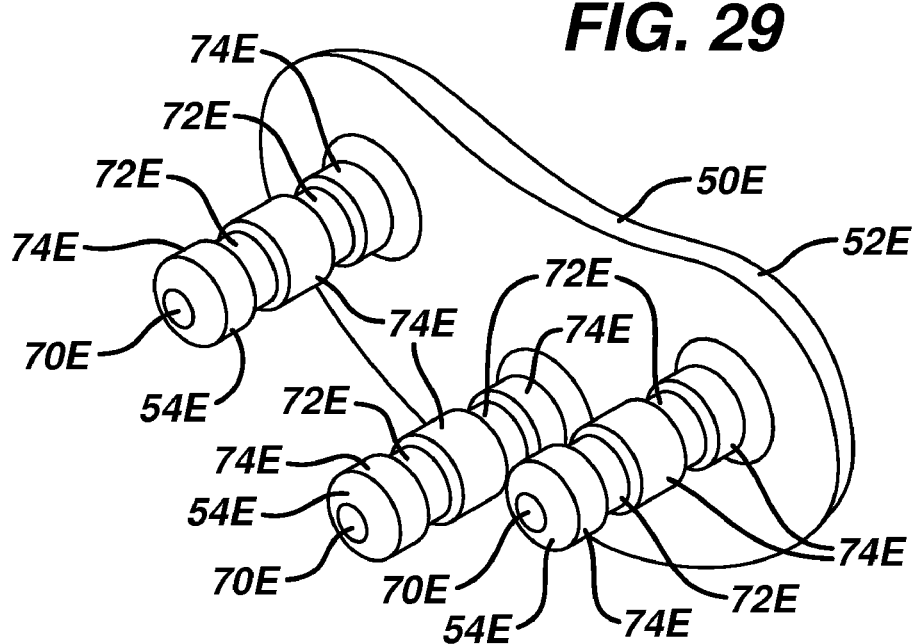
FIG. 29 is perspective view of a fifth embodiment of an anti-abrasion stud.
Figure 30:
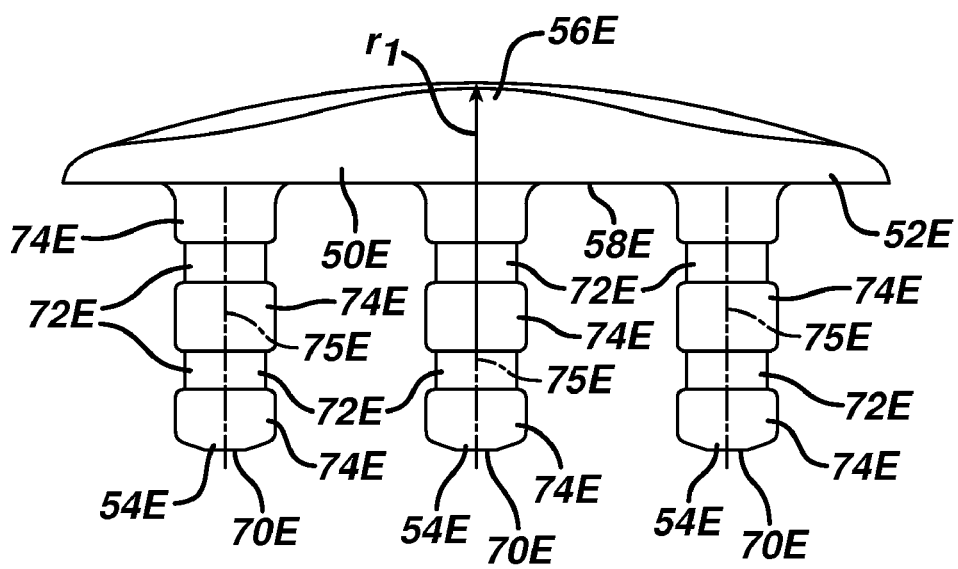
FIG. 30 is an elevation of the anti-abrasion stud of FIG. 29.
Figure 31:
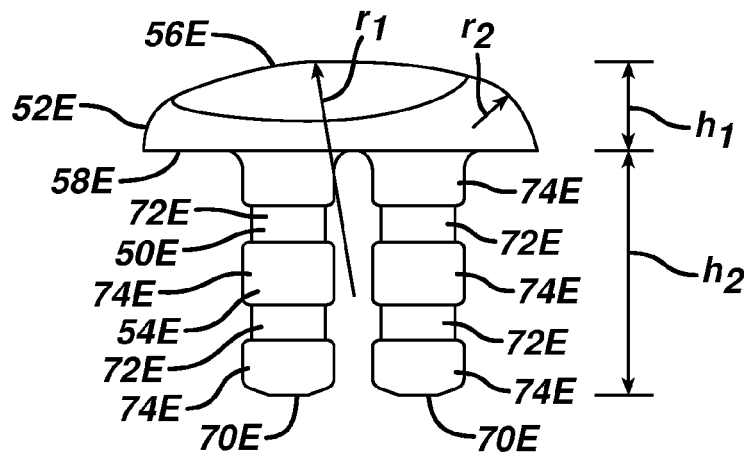
FIG. 31 is a second elevation of the anti-abrasion stud of FIGS. 29-30.
Figure 32:
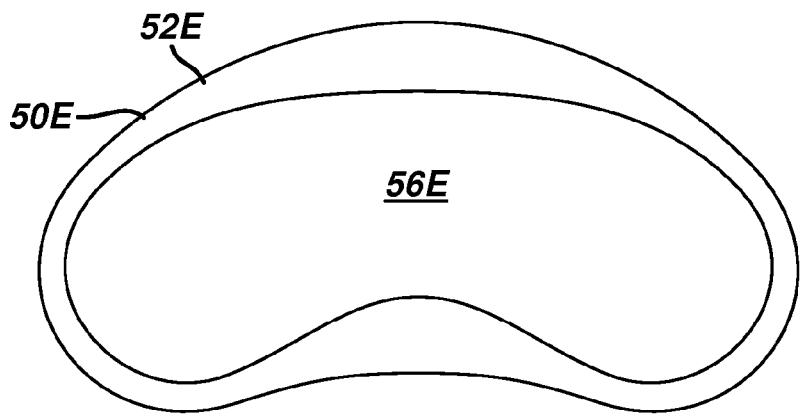
FIG. 32 is a top plan view of the anti-abrasion stud of FIGS. 29-31.
Figure 33:
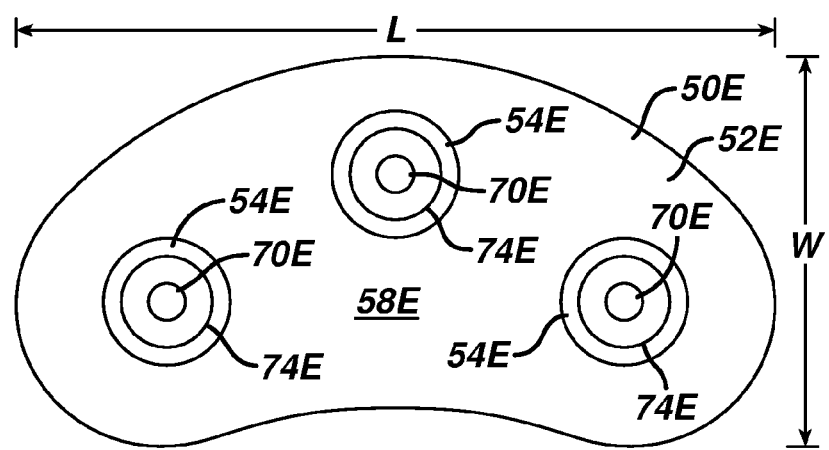
FIG. 33 is a bottom plan view of the anti-abrasion stud of FIGS. 29-32.

As shown in FIGS. 4-6, the illustrated trochlear component 12 has a distal portion 26 that tapers distally and posteriorly; the illustrated uni-condylar femoral component 14 has an anterior portion 28 that tapers proximally and anteriorly. One end of the illustrated trochlear component 12 is implanted adjacent to the intercondylar notch 16. The intercondylar notch 16 remains in its native state, as does a portion 24 of the femoral condyle between the tapering edges of the trochlear component 12 and the uni-condylar femoral component 14 and as do portions 18, 19 of the distal femur adjacent to the intercondylar notch 16. These portions 18, 19, 24 of the femur in their native state include native tissue, such as articular cartilage.

Although not illustrated in the accompanying drawings, it should be understood that the illustrated uni-condylar femoral implant component 14 would be used in conjunction with a uni-condylar tibial implant component. Such a uni-condylar tibial implant component would typically be two-piece, with a metal base and a polymer bearing made of a material such as ultra-high molecular weight polyethylene (UHMWPE), but could be a single integral implant component made out of a material such as UHMWPE.

Figure 1:
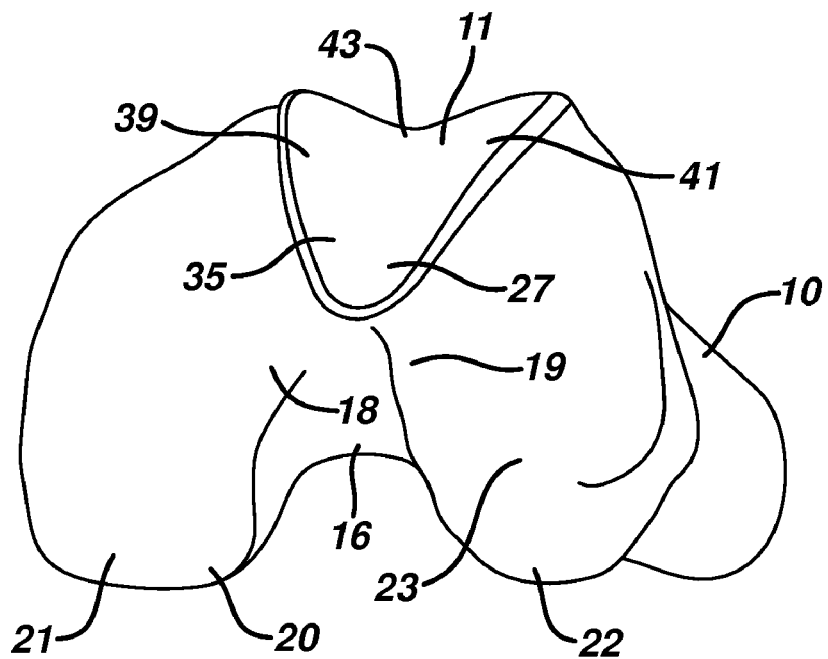
FIG. 1 is a perspective view of a distal femur with an implanted prior art trochlear implant component.
Figure 2:
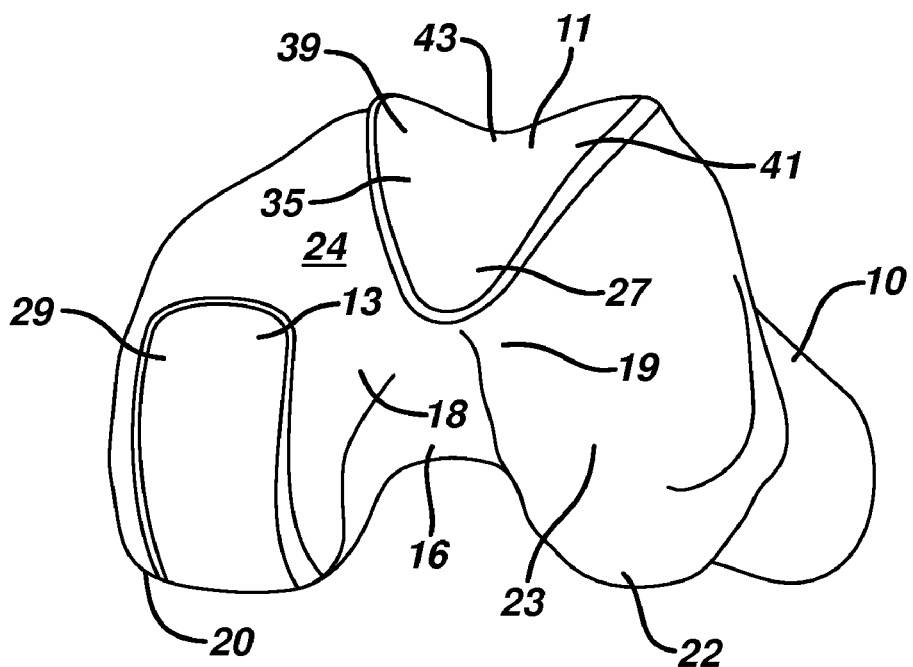
FIG. 2 is a perspective view similar to FIG. 1, showing the distal femur with both a prior art trochlear implant component and a prior art uni-condylar femoral implant component.
Figure 3:
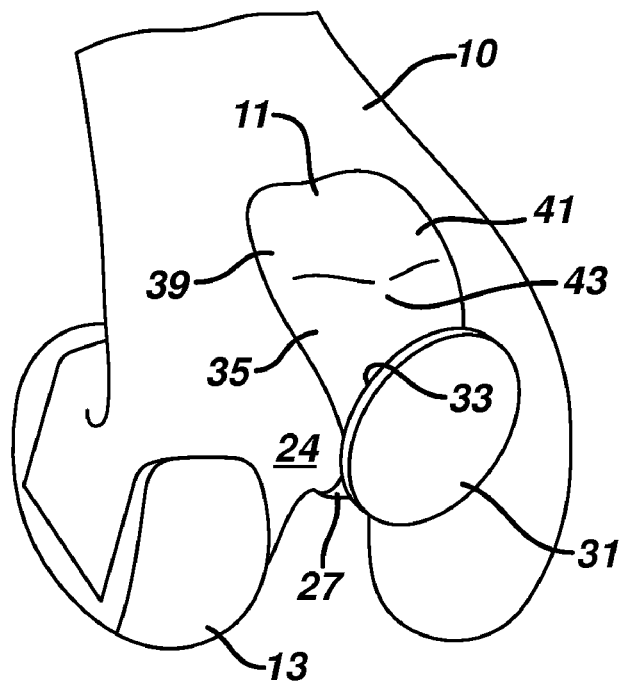
FIG. 3 is a perspective view of a distal femur with both a prior art trochlear implant component and a prior art uni-condylar femoral implant component, showing a prior art patellar implant component bearing against the bearing surface of the trochlear implant component.

When a trochlear component is implanted, the implant system would also typically include a patellar implant component, such as that shown at 30 in FIGS. 3-4. The patellar implant component 30 is sized and shaped to replace a posterior portion of the patella. The patellar implant component has a bearing surface 32 and a bone-facing surface. The illustrated patellar implant component 30 is a two-piece component, with a bearing made out of a smooth material such as (UHMWPE), although the patellar component could be a single integral implant component made out of a material such as UHMWPE.

To protect the area 24 of native tissue between the opposed tapered edges of the distal portion 26 of the trochlear component 12 and anterior portion 28 of the uni-condylar femoral component 14, the orthopaedic implant system of FIG. 5 includes a first embodiment of an anti-abrasion stud 50A implanted at this area 24 of native tissue. To protect the areas 18, 19 of native tissue adjacent the intercondylar notch 16, the orthopaedic implant system of FIG. 6 includes a medial anti-abrasion stud 50B and a lateral anti-abrasion stud 50C implanted at these areas 18, 19. As described in more detail below, other embodiments 50D, 50E of anti-abrasion studs may also be employed to extend the patellar tracking surface and thereby protect native tissue.

All of the illustrated anti-abrasion studs 50A, 50B, 50C, 50D, 50E include common features. As shown in FIGS. 7-33, they each include a head 52A, 52B, 52C, 52D, 52E and a fixation post 54A, 54B, 54C, 54D, 54E. Each head 52A, 52B, 52C, 52D, 52E has a bearing surface 56A, 56B, 56C, 56D, 56E and an opposite bone-facing surface 58A, 58B, 58C, 58D, 58E. The fixation posts 54A, 54B, 54C, 54D, 54E extend outward from the bone-facing surface 58A, 58B, 58C, 58D, 58E of the head 52A, 52B, 52C, 52D, 52E.

The head 52A, 52B, 52C, 52D, 52E of each of the illustrated anti-abrasion stud 50A, 50B, 50C, 50D, 50E is sized and shaped to fit between a portion of the trochlear component 12 and a portion of one uni-condylar femoral implant component 14 without contacting either the trochlear component or the uni-condylar femoral implant component when all of the components are implanted on the distal femur, as illustrated in FIGS. 5-6. As can also be seen from FIGS. 5-33, the head 52A, 52B, 52C, 52D, 52E of each anti-abrasion stud 50A, 50B, 50C, 50D, 50E has a shape that is different from the shape of the bearing surfaces of the trochlear implant component 12 and the uni-condylar femoral implant component 14. Two of the illustrated anti-abrasion studs 50A, 50D have heads that are elliptical in top plan view (see FIGS. 11 and 27); two of the illustrated anti-abrasion studs 50B, 50C have heads that are circular in top plan view (see FIGS. 16 and 19); and one of the illustrated anti-abrasion studs 50E has a head that is kidney-shaped in top plan view (see FIG. 32).

It should be appreciated that the three illustrated shapes for the heads of the anti-abrasion studs are provided as examples only. Alternative shapes may be used and are within the scope of the invention. For example, for anti-abrasion studs that are intended for use to extend the patellar tracking surface further toward the intercondylar notch, the heads of the anti-abrasions studs can have an edge that is shaped to complement the shape of a portion of the edge of the trochlear implant component.

Figure 34:
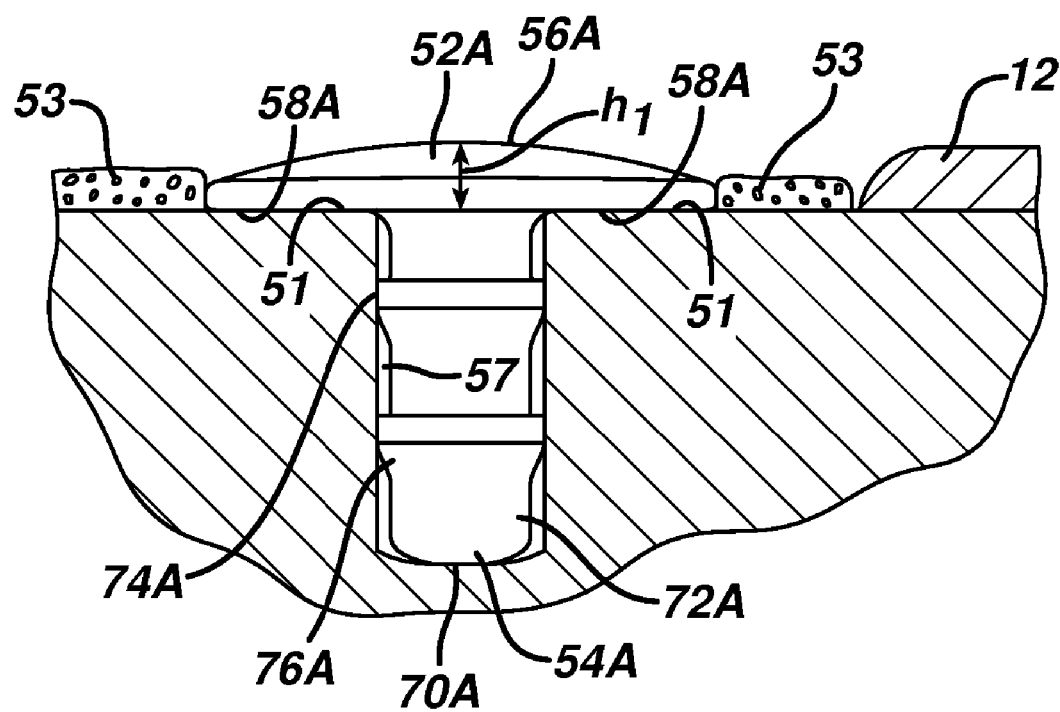
FIG. 34 is a cross-section of a portion of a femur and trochlear implant component, illustrating the position of the first embodiment of the anti-abrasion stud with respect to articular cartilage of the femur.

The head 52A, 52B, 52C, 52D, 52E of each of the illustrated anti-abrasion studs 50A, 50B, 50C, 50D, 50E has a height between the lowest portion of the bone-facing surface 58A, 58B, 58C, 58D, 58E and the highest point on the bearing surface 56A, 56B, 56C, 56D, 56E. These heights are indicated at "$h_1$" in FIGS. 8, 10, 15, 20, 25, 26 and 31. Generally, head heights $h_1$ in the range of about 2-6 mm should be adequate to raise most of the bearing surface 56 of the head 52 above the exterior surface of the articular cartilage on the bone; in other words, the head heights are generally greater than the thickness of the articular cartilage where the anti-abrasion stud is implanted. FIG. 34 illustrates the lowermost point of the bone-facing surface 54A of one of the anti-abrasion studs 50A positioned against the bone surface 51, with a substantial part of the bearing surface 56A of the head 52A above the top level of the articular cartilage 53 surrounding the anti-abrasion stud 50A. A portion of another implant component, such as trochlear component 12, is shown in cross-section in FIG. 34. Examples of numerical values for $h_1$ for the illustrated embodiments are provided in Table 1, below.

The head 52A, 52B, 52C, 52D, 52E of each of the illustrated anti-abrasion studs 50A, 50B, 50C, 50D, 50E has a maximum length and width. These lengths and widths are indicated at "L" and "w" in FIGS. 12, 16, 19, 27 and 33. Examples of numerical values for l and w for the illustrated embodiments are provided in Table 1, below. Examples of numerical values for the perimeters of the illustrated heads are also provided in Table 1 below.

All of the bearing surfaces 56A, 56B, 56C, 56D, 56E of the illustrated anti-abrasion studs 50A, 50B, 50C, 50D, 50E are contoured and substantially smooth, to provide a low friction path for the patellar component during flexion and extension. The illustrated bearing surfaces are convex. The radii of curvature for the bearing surfaces are indicated at "$r_1$" in FIGS. 8, 15, 21, 24, 26 and 30. Examples of numerical values for $r_1$ for the illustrated embodiments are provided in Table 1, below. Examples of surface areas for the bearing surfaces of the illustrated heads are also provided in Table 1 below.

It should be appreciated that the profiles of the bearing surfaces 56A, 56B, 56C, 56D, 56E of the illustrated embodiments are provided as examples only. Various profiles for the bearing surfaces could be used; the most appropriate profile for a bearing surface may relate to the shape of the bearing surface of the implant that the anti-abrasion stud is augmenting or extending. A particular profile or groups of profiles for the bearing surfaces of the anti-abrasion studs can be selected to best augment a wide variety of main implant shapes and sizes. For example, it may be desirable to include a concave portion to form a track. Accordingly, the present invention is not limited to any particular profile for the bearing surfaces of the anti-abrasion studs unless expressly called for in the claims.

The head 52A, 52B, 52C, 52D, 52E of each of the illustrated anti-abrasion studs 50A, 50B, 50C, 50D, 50E has a curved edge 60A, 60B, 60C, 60D, 60E around the perimeter of the bearing surface. The curved edges 60A, 60B, 60C, 60D, 60E extend toward the bone-facing surfaces 58A, 58B, 58C, 58D, 58E. In the illustrated embodiments the curved edges have radii of curvature of about 0.5-5 mm. These radii are indicated at "$r_2$" in FIGS. 8, 10, 14, 15, 20, 21, 24, 26 and 31. Examples of numerical values for $r_2$ for the illustrated embodiments are provided in Table 1, below.

The fixation posts 54A, 54B, 54C, 54D, 54E of each of the illustrated embodiments of anti-abrasion studs 50A, 50B, 50C, 50D, 50E are provided for affixation of the studs to the patient's bone. The illustrated fixation posts are intended to be placed in a prepared bore in the patient's bone, such as the substantially cylindrical bore shown at 57 in FIG. 34, and include raised surface features to aid in affixation of the posts to the walls of the bore 57 in the bone.

Each of the illustrated fixation posts 54A, 54B, 54C, 54D, 54E has a flat, circular end 70A, 70B, 70C, 70D, 70E opposite the head 52A, 52B, 52C, 52D, 52E. The illustrated fixation posts include a plurality of spaced cylindrical portions 72A, 72B, 72C, 72D, 72E having a first diameter and spaced raised cylindrical portions 74A, 74B, 74C, 74D, 74E having a second larger diameter. The cylindrical portions 72A, 72B, 72C, 72D, 72E and raised cylindrical portions 74A, 74B, 74C, 74D, 74E are concentric about the longitudinal axes 75A, 75B, 75C, 75D, 75E of the fixation posts. In the anti-abrasion studs 50A, 50B, 50C, 50D illustrated in FIGS. 7-23, the fixation posts further include conical beveled portions 76A, 76B, 76C, 76D connecting the raised cylindrical portions 74A, 74B, 74C, 74D, to the cylindrical portions 72A, 72B, 72C, 72D. The conical beveled portions 76A, 76B, 76C, 76D are concentric about the longitudinal axes 75A, 75B, 75C, 75D of the fixation posts and taper toward the flat circular ends 70A, 70B, 70C, 70D, of the fixation posts.

The number of fixation posts and the positions of the fixation posts relative to the heads may vary depending on the size and shape of the head. For example, in the first four illustrated anti-abrasion studs 50A, 50B, 50C, 50D, the longitudinal axes of the fixation posts 54A, 54B, 54C, 54D are aligned with the centers of the heads 52A, 52B, 52C, 52D. In the last illustrated anti-abrasion stud 50E, there are three spaced fixation posts 54E positioned to support the head 52E.

Examples of dimensions for the fixation posts 54A, 54B, 54C, 54D, 54E and their surface features 70, 72, 74 are provided in Table 2.

TABLE 2

| Anti-Abrasion Stud Embodiment | Diameter (mm) | | |
|---|---|---|---|
| | Circular end 70 | Smaller diameter cylindrical portion 72 | Larger Diameter cylindrical portion 74 |
| 50A | 2 | 5 | 6 |
| 50B | 2 | 5 | 6 |
| 50C | 2 | 5 | 6 |
| 50D | 2 | 5 | 6 |
| 50E | 2 | 4 | 5 |

It should be understood that the surface features 70, 72, 74 described above are provided as examples only. Other surface features to aid in fixation of the anti-abrasion studs in the bone could be used in addition to or in place of the surface features illustrated and described above. For example, longitudinal

TABLE 1

| Anti-Abrasion Stud Embodiment | Dimension (mm) | | | | | | | |
|---|---|---|---|---|---|---|---|---|
| | "L" | "w" | "$h_1$" | "$h_2$" | "$r_1$" | "$r_2$" | Perimeter | Surface Area (mm²) |
| 50A | 18 | 12 | 2.34 | 12.66 | 30 | 0.5 | 142.4394 | 183.6562 |
| 50B | 10 | 10 | 2.34 | 12.66 | 10 | 1 | 87.2664 | 98.9987 |
| 50C | 10 | 10 | 2.34 | 12.66 | 10 | 1 | 87.2664 | 98.9987 |
| 50D | 20 | 14 | 3.75 | 11.257 | 30 | 2 | 165.8505 | 288.3211 |
| 50E | 41 | 22 | 5 | 13.5 | 30 | 5 | 365.1022 | 857.9848 | surface features could be employed; grooves, ridges or fins could also be used to enhance fixation and retard rotation of the anti-abrasion studs.

It should also be understood that all of the dimensions, areas and radii disclosed herein (including all those set forth in Tables 1 and 2) are provided as examples only. The present invention is not limited to any particular dimension, area or radii unless expressly set forth in the claims.

In four of the illustrated anti-abrasion studs 50A, 50B, 50D, 50E, the entire head 52A, 52B, 52D and 52E and fixation post 54A, 54B, 54D, 54E are integrally-formed. However, the anti-abrasion studs could be made as multi-piece implants that can be assembled in the operating room. The anti-abrasion stud 50C of FIGS. 18-22 is an example of a two-piece anti-abrasion stud, wherein the fixation post 54C includes a flange 80 to which an independent bearing 82 is affixed. Together, the flange 80 and bearing 82 form the head 52C of the stud 50C. The bearing 82 can be affixed to the flange 80 in any standard manner, such as through an interference fit or frictional lock. With such a two-piece stud, a surgical kit could be modular, including a plurality of bearings 82 of different sizes and shapes from which the surgeon may select the most appropriate size and shape for the particular patient.

The anti-abrasion studs 50A, 50B, 50C, 50D, 50E of the present invention may be made of any standard bio-compatible material, although it is preferred that the material be one that is not biodegradable and not bioresorbable. Common metal alloys, such as standard medical implant grade cobalt-chrome alloys and titanium alloys, may be used for the entire implant. In the case of a two-piece anti-abrasion stud 50C of FIGS. 18-22, the fixation post 54C and flange 80 may be made of such a standard material, and the bearing 82 may be made of a different material, such as a ceramic or polymer (for example, ultra-high molecular weight polyethylene), if desired. The entire anti-abrasion stud could also be made of such a ceramic or polymer.

If all or part of the anti-abrasion stud is made of a metal alloy, it may be desirable for the surfaces that will contact bone to be treated to be conducive to bone ingrowth. For example, standard industry can be employed to make the bone-contacting surfaces porous. Coatings may also be employed to induce bone ingrowth into the appropriate portions of the stud or to deliver drugs to the site.

The bearing surfaces 56A, 56B, 56C, 56D, 56E of the anti-abrasion studs preferably provide a low-friction surface for the patellar bearing to move across during the flexion and extension. If the heads 52A, 52B, 52C, 52D, 52E are made of metal, the bearing surfaces may be highly polished to maximize smooth movement of the patellar bearing across the stud bearing surface.

The anti-abrasion studs of the present invention may be provided in the form of implant system, sets or kits. For example, a knee implant system, set or kit could include a set of trochlear components, patellar components and anti-abrasion studs. The system, set or kit could also include uni-condylar femoral implant components and uni-condylar tibial implant components. All of the implant components could be provided in a variety of sizes to accommodate a wide range of patient anatomies. The anti-abrasion studs included in the system, set or kit could include a variety of sizes of a single head shape or a variety of head shapes, profiles and sizes.

To use the anti-abrasion studs 50A, 50B, 50C, 50D, 50E and implant systems of the present invention, the orthopaedic surgeon would prepare the patient's bones in the most appropriate fashion for implantation of the first or major implant components. For example, for a patellofemoral joint arthroplasty, the trochlea of the distal femur would be resected or otherwise shaped or prepared to receive the trochlear implant component and the patella would be resected or otherwise shaped or prepared to receive the patellar implant component (if a patellar implant component is to be used). The trochlear component would then be implanted in a standard manner, as would the patellar implant component, if used. For a tibiofemoral joint arthroplasty, one or both of the femoral condyles would be resected or otherwise shaped or prepared to receive an appropriate uni-condylar femoral implant component and the corresponding side of the tibial plateau would be resected or otherwise shaped or prepared to receive an appropriate tibial implant component (or assembly of components). The femoral uni-condylar implant component or components and the uni-condylar tibial component or components would then be implanted in a standard manner.

If the surgeon determines at the time of the original surgery that the patient would benefit from providing an enhanced or augmented patellar track extending further toward the intercondylar notch, or that the transition between the bearing surfaces of the trochlear component and the uni-condylar femoral component or components is uneven or overly extended, the surgeon may chose to use one of the anti-abrasion studs of the system to extend the bearing surfaces of the other implant components.

The orthopaedic surgeon may select the most appropriate size and shape of anti-abrasion stud to extend the bearing surface or surfaces. Preferably, the head of the anti-abrasion stud is sized and shaped so that it will not contact any part of the trochlear implant component or uni-condylar femoral implant component. A drill or reamer is then used to prepare a bore in the bone; preferably, the outer diameter of the drill or reamer is slightly less than the outer diameter of the fixation feature (such as larger diameter portion 74) of the fixation post. The fixation post is then introduced into the bore and pushed into the bore until the lowermost part of the head (such as the bone-facing portion) contacts the surface of the bone. At least a substantial part of the bearing surface of the head will be above the level of the articular cartilage. This procedure may be repeated with additional anti-abrasion studs as deemed necessary by the surgeon.

If the orthopaedic surgeon initially elects to avoid using the anti-abrasion studs, the studs may be implanted in a separate procedure on a later date. For example, if the patient has received a trochlear implant or a uni-condylar femoral implant and complains of pain or of a patellar component catching or making a noise during flexion or extension, the surgeon may opt to implant an anti-abrasion stud at that time. Due to the small size of the anti-abrasion studs, this subsequent procedure can be a minimally invasive one.

Thus, the system of the present invention provides the surgeon with the opportunity to enhance and extend the bearing surfaces of standard uni-compartmental implant components to fit the needs of individual patients. The anti-abrasion stud will provide an additional bearing surface that substantially bridges a portion of the gap between the other implant components to provide an augmented bearing surface and covers and protects the native articular cartilage from abrasion.

While only specific embodiments of the invention have been described and shown, it is apparent that various alternatives and modifications can be made thereto. Moreover, those skilled in the art will also recognize that certain additions can be made to these embodiments. It is, therefore, the intention in the appended claims to cover all such alternatives, modifications and additions as may fall within the true scope of the invention.

I claim:

1. A method of repairing a knee joint comprising:
   implanting a trochlear component on the femur, the trochlear component having a tapered distal portion and a bearing surface comprising two convex surfaces meeting along a groove, the trochlear component being implanted adjacent to the intercondylar notch of the femur;
   implanting a patellar component on the patella;

providing a stud having a bearing surface, a bone-facing surface and a fixation post extending outward from the bone-facing surface;

implanting the stud on the femur adjacent to native articular cartilage so that at least a substantial portion of the bearing surface of the stud stands above the top surface of the adjacent native articular cartilage and the fixation post extends into the bone of the femur;

wherein the stud and trochlear component are discrete components and are sized, shaped and positioned to limit contact between the patellar component and the native articular cartilage around the trochlear component during flexion and extension of the knee joint and wherein the stud and trochlear component are both present on the femur at the same time;

wherein the trochlear component and patellar component are sized, shaped and positioned so that the patellar component articulates with the bearing surface of the trochlear component;

wherein there is no contact between the bearing surface of the stud and the bearing surface of the trochlear component; and wherein the bearing surface of the stud is made of a material that is not biodegradable and not bioresorbable.

2. The method of claim 1 wherein the stud is implanted adjacent to the trochlear groove.

3. The method of claim 1 wherein the step of implanting the trochlear component and the step of implanting the stud are performed in separate surgical procedures.

4. The method of claim 1 wherein the step of implanting the trochlear component and the step of implanting the stud are performed in a single surgical procedure.

5. The method of claim 1 further comprising the step of implanting a uni-condylar component on one of the condyles of the distal femur, and wherein the uni-condylar component, the stud and the trochlear component are all present on the femur at the same time and the uni-condylar component and the stud are spaced from each other.

6. The method of claim 5 wherein the stud is implanted between the trochlear component and the uni-condylar component and wherein there is no contact between the stud and the uni-condylar component.

7. The method of claim 5 wherein the step of implanting the uni-condylar component and the step of implanting the trochlear component are performed in separate surgical procedures.

8. The method of claim 5 wherein the step of implanting the uni-condylar component, the step of implanting the trochlear component and the step of implanting the stud are performed in three separate surgical procedures.

9. The method of claim 1 wherein
the trochlear component is implanted adjacent to native articular cartilage.

10. The method of claim 9 further comprising the step of implanting a uni-condylar component on one of the condyles of the distal femur, the uni-condylar having an arcuate bearing surface and covering the distal and posterior articulating surfaces of one femoral condyle, wherein the uni-condylar component, the stud and the trochlear component are all present on the femur at the same time and wherein the stud is implanted between and spaced from the trochlear component and the uni-condylar component.

11. The method of claim 10 wherein the bearing surface of the stud is made of a material selected from the group consisting of metal, polymer and ceramic.

12. The method of claim 11 wherein the entire stud is made of a material selected from the group consisting of metal, polymer and ceramic.

13. The method of claim 1 wherein the bearing surface of the stud is made of a material selected from the group consisting of metal, polymer and ceramic.

14. The method of claim 13 wherein the entire stud is made of material selected from the group consisting of metal, polymer and ceramic.

* * * * *